United States Patent
Levine

(10) Patent No.: US 10,314,779 B2
(45) Date of Patent: Jun. 11, 2019

(54) COMPOSITION FOR TRANSDERMAL DELIVERY OF GLUTATHIONE

(71) Applicant: Rachel Sarah Levine, Victoria (CA)

(72) Inventor: Rachel Sarah Levine, Victoria (CA)

( * ) Notice: Subject to any disclaimer, the term of this patent is extended or adjusted under 35 U.S.C. 154(b) by 178 days.

(21) Appl. No.: 15/604,144

(22) Filed: May 24, 2017

(65) Prior Publication Data

US 2018/0338906 A1    Nov. 29, 2018

(51) Int. Cl.
| | | |
|---|---|---|
| *A61K 9/00* | (2006.01) |
| *A61K 9/70* | (2006.01) |
| *A61K 31/59* | (2006.01) |
| *A61K 38/06* | (2006.01) |
| *A61K 47/10* | (2017.01) |
| *A61K 31/198* | (2006.01) |

(52) U.S. Cl.
CPC .......... *A61K 9/0014* (2013.01); *A61K 9/7023* (2013.01); *A61K 31/198* (2013.01); *A61K 31/59* (2013.01); *A61K 38/063* (2013.01); *A61K 47/10* (2013.01)

(58) Field of Classification Search
CPC ...... A61K 38/063; A61K 47/10; A61K 47/12; A61K 47/20; A61K 9/0014
See application file for complete search history.

(56) References Cited

U.S. PATENT DOCUMENTS

2008/0260653 A1* 10/2008 Buttar .................... A61K 47/10
                                                514/1.1

* cited by examiner

*Primary Examiner* — Kortney L. Klinkel
(74) *Attorney, Agent, or Firm* — Buskop Law Group, P.C.; Wendy Buskop

(57) ABSTRACT

A transdermal formulation which can be applied to the skin as a latex-free hypoallergenic adhesive patch or transdermal delivery cream using a combination of glutathione, Vitamin D, glycol, sodium bicarbonate and base cream resilient in the presence of a wide range of drugs while increasing permeation of active antioxidant agents, water, isopropyl myristate, polyoxyethylene sorbitan monooleate, isopropyl palmitate, ascorbic acid, and dimethyl sulfoxide. The dosage amount can create in the patient (i) regulation of sleep, (ii) increased energy during awake periods, (iii) improved concentration during awake periods, (iv) reduction of facial wrinkles, and (v) reduction of joint and muscular pain with increases by at least 10 percent of the ability of skin to retain moisture and totally absorb the glutathione without requiring injection or oral supplementation of the glutathione.

25 Claims, 11 Drawing Sheets

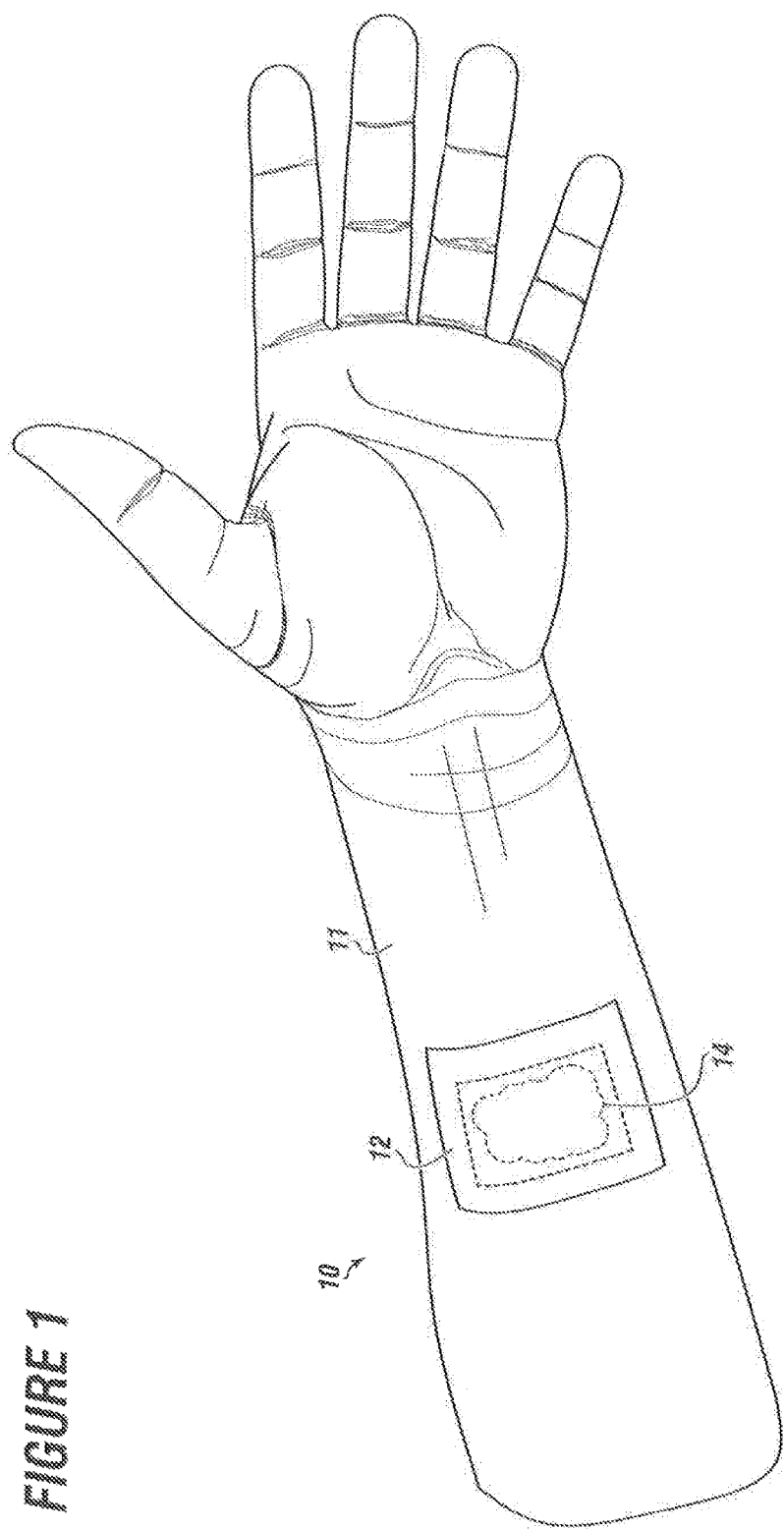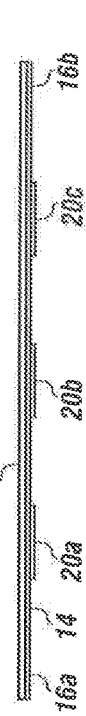

FIGURE 3

| Formulation 4 | Weight Percent (wt%) |
|---|---|
| Glutathione | 10 wt% |
| Lecithin | 20 wt % |
| Isopropyl Palmitate | 60 wt% |
| Lauric Acid | 5 wt% |
| Coconut Oil | 3 wt% |
| Palm Kernel Oil | 2 wt% |
| Total | 100 wt% |

FIGURE 4

| Formulation 5 | Weight Percent (wt%) |
|---|---|
| Glutathione | 10 wt% |
| Lecithin | 40 wt% |
| Isopropyl Palmitate | 50 wt% |
| Total | 100 wt% |

FIGURE 5

| Formulation 6 | Weight Percent (wt%) |
|---|---|
| Glutathione | 10 wt% |
| Lecithin | 50 wt% |
| Isopropyl Palmitate | 30 wt% |
| Arnica Montana | 2 wt% |
| Lauric Acid | 3 wt% |
| Coconut Oil | 2 wt% |
| Palm Kernel Oil | 3 wt% |
| Total | 100 wt% |

FIGURE 6

| Formulation 7 | Weight Percent (wt%) |
|---|---|
| Glutathione | 10 wt% |
| Lecithin | 40 wt% |
| Isopropyl Palmitate | 40 wt% |
| Lauric Acid | 6 wt% |
| Coconut Oil | 3 wt% |
| Palm Kernel Oil | 1 wt% |
| Total | 100 wt% |

FIGURE 7

| Formulation 8 | Weight Percent (wt%) |
|---|---|
| Aqua (purified water) | 61.490 wt% |
| Glycerine | 3.00 wt% |
| Xanthan Gum | 0.610 wt% |
| Isopropyl Myristate | 3.00 wt% |
| Stearyl Alcohol | 3.50 wt% |
| Caprylic/Capric Triglycerides | 3.00 wt% |
| Cetearyl Alcohol (and) Ceteareth-20 | 6.00 wt% |
| Arnica Montana | 5.00 wt% |
| Dimethicone (Polydimethylsiloxane) | 3.00 wt% |
| Cetyl Alcohol | 3.00 wt% |
| Soy lecithin | 2.00 wt% |
| Glutathione | 5.00 wt% |
| Focus Blend EO | 0.20 wt% |
| Phenoxyethanol, Caprylyl Glycol | 1.20 wt% |
| Total | 100 wt% |

FIGURE 8

| Formulation 9 | Weight Percent (wt%) |
|---|---|
| Aqua (purified water) | 61.61 wt% |
| Glycerine | 3.00 wt% |
| Xanthan Gum | 0.650 wt% |
| Isopropyl Myristate | 3.00 wt% |
| Cetearyl Alcohol (and) Ceteareth-20 | 6.00 wt% |
| Caprylic/Capric Triglycerides | 3.00 wt% |
| Stearyl Alcohol | 3.50 wt% |
| Cetyl Alcohol | 3.00 wt% |
| Dimethicone (Polydimethylsiloxane) | 2.00 wt% |
| Calendula Oil | 3.00 wt% |
| Soy lecithin | 5.00 wt% |
| Glutathione | 5.00 wt% |
| Rose Absolute | 0.04 wt% |
| Phenoxyethanol, Caprylyl Glycol | 1.20 wt% |
| Total | 100.00 wt% |

FIGURE 9

| Formulation 10 | Weight Percent (wt%) |
|---|---|
| Glutathione | 7 wt% |
| Vitamin D | 3 wt% |
| Glycol | 20 wt% |
| Sodium Bicarbonate | 10 wt% |
| Lecithin | 40 wt% |
| Isopropyl Palmitate | 20 wt% |
| Total | 100 wt% |

FIGURE 10

| Formulation 11 | Weight Percent (wt%) |
|---|---|
| Glutathione | 10 wt% |
| Water | 85 wt% |
| Sodium Bicarbonate | 4 wt% |
| Propylene Glycol | 1 wt% |
| Total | 100 wt% |

FIGURE 11

| Formulation 12 | Weight Percent (wt%) |
|---|---|
| Glutathione | 10 wt% |
| Water | 61 wt% |
| Sodium Bicarbonate | 9 wt% |
| Polyoxyethylene sorbitan monooleate | 5 wt% |
| Ascorbic Acid | 5 wt% |
| Dimethyl sulfoxide | 10 wt% |
| Total | 100 wt% |

FIGURE 12

| Formulation 13 | Weight Percent (wt%) |
|---|---|
| Glutathione | 10 wt% |
| Vitamin D | 3 wt% |
| Glycol | 20 wt% |
| Sodium Bicarbonate | 9 wt% |
| Lecithin | 29 wt% |
| Isopropyl Palmitate | 29 wt% |
| Total | 100 wt% |

FIGURE 13

| Formulation 14 | Trade Name | Weight Percent (wt%) |
|---|---|---|
| Purified Water | Purified Water | 63.55 |
| Glycerine | Glycerine | 3.00 |
| Xanthan Gum | Ketrol CG SFT | 0.65 |
| Isopropyl Myristate | Isopropyl Myristate | 3.00 |
| Cetearyl Oliviate, Sorbitan Olivate | Olivem 100 | 6.00 |
| Caprylic/Capric Triglycerides | Jeechem CTG | 3.00 |
| Stearyl Alcohol | Stearyl Alcohol | 3.50 |
| Cetyl Alcohol | Cetyl Alcohol | 3.00 |
| Helianthus Annuus (Sunflower) Seed Oil | Jeesilc PDS-350 | 2.00 |
| Soy lecithin | Soy lecithin | 5.00 |
| Glutathione | L-Glutathione Reduced | 5.00 |
| Essential Oil | Essential Oil | 0.50 |
| Gluconolactone, Sodium Benzoate | Geogard Ultra | 1.50 |
| Glyceryl Caprylate | Dermosoft GMCY | 0.30 |
| Total | | 100.00 |

FIGURE 14

| Formulation 15 | Trade Name | Weight Percent (wt%) |
|---|---|---|
| Purified Water | Purified Water | 58.55 |
| Glycerine | Glycerine | 3.00 |
| Xanthan Gum | Keltrol CG SFT | 0.65 |
| Isopropyl Myristate | Isopropyl Myristate | 3.00 |
| Cetearyl Oliviate, Sorbitan Olivate | Olivem 1000 | 6.00 |
| Caprylic/Capric Triglycerides | Jeechem CTG | 3.00 |
| Stearyl Alcohol | Stearyl Alcohol | 3.50 |
| Cetyl Alcohol | Cetyl Alcohol | 3.00 |
| Arnica Montana Oil | Arnica Montana Oil (Infused Almond Oil) #7160 | 5.00 |
| Helianthus Annuus (Sunflower) Seed Oil | Jeesilc PDS-350 | 2.00 |
| Soy lecithin | Soy lecithin | 5.00 |
| Glutathione | L-Glutathione Reduced | 5.00 |
| Essential Oil | Essential Oil | 0.50 |
| Gluconolactone, Sodium Benzoate | Geogard Ultra | 1.50 |
| Glyceryl Caprylate | Dermosoft GMCY | 0.30 |
| Total | | 100.00 |

FIGURE 15

| Formulation 16 | Weight Percent (wt%) |
|---|---|
| Purified Water | 58.55 |
| Glycerine | 3.00 |
| Xanthan Gum | 0.60 |
| Isopropyl Myristate | 3.50 |
| Cetearyl Oliviate, Sorbitan Olivate | 6.00 |
| Caprylic Triglycerides | 3.50 |
| Stearyl Alcohol | 3.00 |
| Cetyl Alcohol | 3.50 |
| Arnica Montana Oil | 2.00 |
| Heliatnthus Annus (Sunflower Seed Oil) | 2.05 |
| Soy Lecithin | 5.00 |
| Glutathione | 7.00 |
| Essential Oil | 0.50 |
| Gluconolactone, Sodium Benzonate | 1.50 |
| Glyceryl Caprylate | 0.30 |
| Total | 100.00 |

FIGURE 16

| Formulation 17 | Weight Percent (wt%) |
|---|---|
| Purified Water | 61.55 |
| Glycerine | 3.00 |
| Xanthan Gum | 0.65 |
| Isopropyl Myristate | 3.00 |
| Cetearyl Oliviate, Sorbitan Olivate | 6.00 |
| Caprylic Triglycerides | 3.00 |
| Stearyl Alcohol | 3.50 |
| Cetyl Alcohol | 3.20 |
| Heliatnthus Annus (Sunflower Seed Oil) | 3.80 |
| Soy Lecithin | 4.00 |
| Glutathione | 6.00 |
| Essential Oil | 0.50 |
| Gluconolactone, Sodium Benzonate | 1.50 |
| Glyceryl Caprylate | 0.30 |
| Total | 100.00 |

COMPOSITION FOR TRANSDERMAL DELIVERY OF GLUTATHIONE

CROSS REFERENCE TO RELATED APPLICATIONS

The present application claims priority to and the benefit of U.S. Provisional Patent Application Ser. No. 62/341,562 filed on May 25, 2016, entitled "COMPOSITION FOR TRANSDERMAL DELIVERY OF GLUTATHIONATE". This reference is hereby incorporated in its entirety.

FIELD

The present embodiments generally relate to a composition for transdermal delivery of glutathione.

BACKGROUND

A need exists for a transdermal delivery system for glutathione to reduce nausea in patients.

The present embodiments meet these needs.

BRIEF DESCRIPTION OF THE FIGURE

The detailed description will be better understood in conjunction with the accompanying drawings as follows:

FIG. 1 depicts a transdermal delivery system according to one or more embodiments.

FIG. 2 depicts a detail of the latex-free hypoallergenic adhesive patch according to one or more embodiments.

FIG. 3 depicts Formulation 4 according to one or more embodiments.

FIG. 4 depicts Formulation 5 according to one or more embodiments.

FIG. 5 depicts Formulation 6 according to one or more embodiments.

FIG. 6 depicts Formulation 7 according to one or more embodiments.

FIG. 7 depict Formulation 8 according to one or more embodiments.

FIG. 8 depicts Formulation 9 according to one or more embodiments.

FIG. 9 depicts Formulation 10 according to one or more embodiments.

FIG. 10 depicts Formulation 11 according to one or more embodiments.

FIG. 11 depicts Formulation 12 according to one or more embodiments.

FIG. 12 depicts Formulation 13 according to one or more embodiments.

FIG. 13 depicts Formulation 14 according to one or more embodiments.

FIG. 14 depicts Formulation 15 according to one or more embodiments.

FIG. 15 depicts Formulation 16 according to one or more embodiments.

FIG. 16 depicts Formulation 17 according to one or more embodiments.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments generally relate to a composition for transdermal delivery of glutathione.

The present embodiment further relate to a transdermal formulation which can be applied as a latex-free hypoallergenic adhesive patch or transdermal delivery cream using a combination of glutathione, Vitamin D, arnica, glycol, a buffer and a base cream resilient in the presence of a wide range of drugs while increasing permeation of active antioxidant agents, water, isopropyl myristate, polyoxyethylene sorbitan monooleate, isopropyl palmitate, ascorbic acid, and dimethyl sulfoxide.

In embodiments, the buffer can be sodium bicarbonate with a pH from 5-8.

For patients unable to take antioxidants and vitamins in more common forms, such as pills and injections, the use of a transdermal formulation can often mean the difference between treatment success or treatment failure.

In embodiments, transdermal formulation can be administered as a transdermal delivery cream or in the form of a latex-free hypoallergenic adhesive patch allowing antioxidants and vitamins to successfully penetrate the skin.

Also, vitamin D can improve absorption of glutathione.

In embodiments, the transdermal formulation can avoid many common side effects of drugs, such as upset stomach, and minimize the effects on other organs.

For example, the reduction of side effects is particularly significant in sleep treatment, where the application of the formulation can be localized to an area with relatively low blood-flow. Therefore, higher concentrations at the site of application and lower concentrations of the drug throughout the body enable a patient to restfully stay asleep.

A benefit of the embodiments is that the transdermal formulation can help prevent an early onset of aging and cancer in patients, which can cause an accelerated death. The embodiments can help save lives by providing preventive care to patients to avoid life threatening illness.

The transdermal formulation can be a hypoallergenic delivery system. In embodiments, the transdermal formulation can use a delivery system that is latex-free. Latex is a toxic material, which can be harmful to the environment and cause some individuals to have a significant allergic reaction, such as irritating itchy rashes and even anaphylactic shock.

The embodiments can provide an easy to apply latex-free hypoallergenic adhesive patch that does not require special nursing skills or child proof containers. The package can be easily opened from a vacuum sealed sleeve.

The embodiments can provide a drug delivery system, which can prevent individuals from choking on the medication.

In embodiments, the invention can be a transdermal formulation in a carrier, such as a cream, a gel or a foam. For example, the transdermal formulation as a cream can be 0.1 weight percent to 5 weight percent glutathione and 0.1 weight percent to 5 weight percent aloe. An example of the transdermal formulation of a gel can be 0.1 weight percent to 5 weight percent glutathione, 0.5 weight percent to 5 weight percent aloe, and 0.5 weight percent to 5 weight percent arnica. An example of the transdermal formulation as a foam can be 0.1 weight percent to 5 weight percent glutathione, 0.5 weight percent to 5 weight percent Vitamin D, and 0.5 weight percent to 3 weight percent aloe.

In embodiments, the glutathione can be a powder.

In embodiments, the latex-free hypoallergenic adhesive patch can have a first side and a second side. In embodiments, the latex-free hypoallergenic adhesive patch can be from 1 centimeter×1 centimeter to 3 centimeters×3 centimeters. In embodiments, the transdermal formulation and a magnesium component can be disposed on the same side of the latex-free hypoallergenic adhesive patch.

In embodiments, the type of adhesive used for the latex-free hypoallergenic adhesive patch can be an acrylic adhesive.

The latex-free hypoallergenic adhesive patch can be formed from a continuous sheet of a type of closed cell foam, known as polyethylene foam, which can be very thin such as from 0.001 millimeters to 0.2 millimeters in thickness.

In embodiments, a layer of adhesive can be disposed on the closed foam in a thickness from 0.001 millimeters to 0.01 millimeters. The adhesive can be an easily removable adhesive that does not cause rashes or otherwise aggravate the patient's skin. Also, the adhesive can be waterproof.

In embodiments, the latex-free hypoallergenic adhesive patch can be a reservoir patch with an absorbent pad and foam on the back or a monolithic patch.

In embodiments, a therapeutically effective amount of the transdermal formulation can be three different formulations.

Formulation 1:

In embodiments, the first formulation can have 4 weight percent to 10 weight percent glutathione, 0.5 weight percent to 3 weight percent Vitamin D, with no less than 1 unit and no more than 5000 units, 18 weight percent to 20 weight percent glycol, 3 weight percent to 9 weight percent sodium bicarbonate and 47 weight percent to 58 weight percent base cream that is resilient in the presence of a wide range of drugs while increasing permeation of active antioxidant agents.

In embodiments, a strip of magnesium glycinate can be attached on the first formulation. In embodiments, the strip of magnesium glycinate can be one continuous strip that extends across the entire formulation. In embodiments, the magnesium glycinate can be installed on the formulation as a series of strips, which can be offset from each other. The strip of the magnesium glycinate can be from ¼ centimeters to 10 centimeters in length, from 0.25 centimeters to 15 centimeters in width and can cover from 1 percent to 100 percent of the latex-free hypoallergenic adhesive patch.

In embodiments, the 1 weight percent to 20 weight percent magnesium glycinate can be added to the transdermal delivery cream and a latex-free hypoallergenic adhesive patch.

The embodiments can provide a dosage amount of the formulation either in a transdermal delivery cream or on the latex-free hypoallergenic adhesive patch for delivery to a patient over a unit of time, such as from at least 24 hours to 48 hours.

The dosage amount creates in the patient (i) regulation of sleep, (ii) increased energy during awake periods, (iii) improved concentration during awake periods, (iv) reduction of facial wrinkles, and (v) reduction of joint and muscular pain, which can increase by at least 10 percent the ability of skin to retain moisture and totally absorb the glutathione without requiring an injection or oral supplementation of the glutathione.

The following example depicts the therapeutic effects of the invention using formulation 1.

Formulation 1—Example 1

Bill, a 45 year old male, weighing 220 pounds and having Type 1 diabetes fasted from Midnight to 8:00 am prior to application of the transdermal delivery system. Under a strong light at approximately 8:00 am, a baseline of wrinkles was visually computed as 2.2 wrinkles per side of his face for a total of 44 wrinkles.

The transdermal delivery system with formulation 1 can use the following weight percents: 10 weight percent glutathione, 2 weight percent Vitamin D (1000 units), 19 weight percent glycol, 3.5 weight percent sodium bicarbonate, and 55.5 weight percent base cream was used.

In embodiments, formulation 1 can include 1 weight percent to 5 weight percent arnica.

Formulation 1 on the latex-free hypoallergenic adhesive patch was applied to Bill's right forearm between the wrist and elbow for 46 hours.

After 46 hours, the latex-free hypoallergenic adhesive patch was removed at approximately 11:00 am and the wrinkle count was found to be reduced to about 10 percent, which is a total 39 wrinkles +/−5 percent.

Formulation 1—Example 2

Mary, a 50 year old woman, weighing 135 pounds and having a significant amount of early onset wrinkles due to an immense amount of personal stress and too much sun exposure over an extensive period of time. Mary fasted from 10:00 pin until 6:00 am before the application of transdermal delivery cream to her face. Under a strong light at 6:00 am a base line of deep wrinkles around the upper cheeks and crows lines between the eyebrows was visually computed as 15 deep wrinkles per side of her upper face near eyes and between eyebrows for a total of 30 wrinkles.

The transdermal delivery cream of formulation 1 can use the following weight percent: 5 weight percent glutathione, 2 weight percent Vitamin D (1000 units), 18 weight percent glycol, 3.5 weight percent sodium bicarbonate, and 46.5 weight percent base cream was used.

In embodiments, formulation 1 can include 1 weight percent to 5 weight percent arnica and aloe.

After washing her face each time, the transdermal delivery cream was applied at 6:00 am each morning and 10:00 pm each evening.

The transdermal delivery cream application was halted after 48 hours at approximately 10:00 pm. On the following morning at 6:30 am, the wrinkle count was found to have been reduced by 7 percent around the between the eyebrow and upper cheeks to a total of 9 wrinkles on each side and reduction of depths of the wrinkles by 5 percent.

Formulation 1—Example 3

Fred, a 75 year old man weighing 175 pounds, has a significant amount of scrofulous eczema on the upper part of his face, ears and hairline. Fred has a history of excessive drinking and smoking for at least 30 years. Fred has suffered persistent flaking and itching from the eczema for many years. Fred fasted from 11:00 pm until 7:00 am the following morning, with only an intake of 1 glass of water in the middle of the night prior to the transdermal delivery system. Under a strong light, it was noted that there were red patches, which had raised bumps on the upper cheeks below the eyes, red flaking patches along both sides of the hairline and redness on upper parts of his ears.

The latex-free hypoallergenic adhesive patch of formulation 1 can use the following weight percents: 10 weight percent glutathione, 3 weight percent Vitamin D (2000 units), 20 weight percent glycol, 15 weight percent sodium bicarbonate, and 61.5 weight percent base cream was used.

In embodiments, formulation 1 can include 1 weight percent to 5 weight percent arnica.

The latex-free hypoallergenic adhesive patch was applied at 7:15 am to the under part of his upper left arm.

The latex-free hypoallergenic adhesive patch was removed after 48 hours at approximately 7:00 am and the reduction of redness subsided by 30 percent. The scrofulous flaking was reduced by 17 percent especially in the highly affected areas along the hairline and the upper cheeks. The itching was reduced by 20 percent giving significant relief during the 48 hours of wearing the transdermal delivery system.

It should be noted that formulation 1 does not only affect wrinkles, but can reduce the time of healing for burns and prevent oxidative stress. Oxidative stress is an imbalance between the production of free radicals and the ability of the body to counteract or detoxify their harmful effects through neutralization by antioxidants.

Additionally, it should be noted that formulation 1 can assist in eczema treatment.

In embodiments, formulation 1 can be used for skin lightening.

Formulation 2

In embodiments, the second formulation can have 4 weight percent to 10 weight percent glutathione, 75 weight percent to 85 weight percent water, 3 weight percent to 9 weight percent sodium bicarbonate, and 0.1 weight percent to 1 weight percent propylene glycol.

In embodiments, formulation 2 can include 1 weight percent to 5 weight percent arnica.

Formulation 2—Example 1

Sally is a 60 year old woman who has had difficulty falling sleeping for two years since the death of her husband. Consistently, Sally cannot fall asleep before 12:00 am even though she retires at 10:00 pm. In turn, Sally's energy dips at 2:00 pm each afternoon, approximately two hours after she eats lunch.

The latex-free hypoallergenic adhesive patch of formulation 2 can use the following weight percents: 10 weight percent glutathione, 83 weight percent water, 3.5 weight percent sodium bicarbonate, and 1.5 weight percent propylene glycol.

In embodiments, formulation 2 can include 1 weight percent to 5 weight percent arnica.

The latex-free hypoallergenic adhesive patch was administered at 6:30 am, and she wore the latex-free hypoallergenic adhesive patch for 45 hours. Sally reported that her energy at 2:00 pm increased by 12 percent the first day and about 20 percent on the second day. Her sleep improved significantly, and she was able to fall asleep one-half hour after retiring to bed at 10:00 pm. Therefore, Sally had a significant improvement of 90 percent.

Formulation 2—Example 2

Jessica is a 25 year old woman who wakes up consistently at 5:00 am and is unable to fall back asleep. Her energy dips at 4:00 pm during the day, but she gets another burst of energy at 9:00 pm preventing her from getting the requisite amount of sleep.

The transdermal delivery cream of formulation 2 can use the following weight percents: 9 weight percent glutathione, 84.5 weight percent water, 3.5 weight percent sodium bicarbonate, and 1.5 weight percent propylene glycol.

In embodiments, formulation 2 can include 1 weight percent to 5 weight percent arnica.

The transdermal delivery cream was administered at 9:00 pm and again at 7:30 am for 48 hours on the temples of her face as well on her chest. Jessica reported that she did wake at 5:00 am both mornings hut was able to fall back asleep fairly quickly and woke at 6:30 am feeling more refreshed. Her energy at 4:00 pm was increased by 30 percent both days and her 9:00 pm burst of energy subsided by 40 percent allowing her to fall asleep at 10:30 pm. Therefore, providing Jessica with almost a solid eight hours of sleep for 48 hours.

Formulation 2—Example 3

Malcolm is a 45 year old man who has celiac disease. He falls asleep almost instantly when he lies down at 10:00 pm. He consistently wakes at 2:00 am and can only fall back asleep at 4:30 am. He needs to wake up at 6:00 am for work. His energy dips consistently each day between 3:00 pm and 6:00 pm.

The latex-free hypoallergenic adhesive patch of formulation 2 can use the following weight percents: 10 weight percent glutathione, 84.5 weight percent water, 4 weight percent sodium bicarbonate, and 1.5 weight percent propylene glycol.

The latex-free hypoallergenic adhesive patch was administered at 9:30 am, and he wore the latex-free hypoallergenic adhesive patch for 48 hours. Malcolm reported that he woke up once the first night at 2:00 am, but fell back asleep almost immediately and slept through the night completely the second night.

Malcolm also reported that his energy was 50 percent better throughout both days of wearing the latex-free hypoallergenic adhesive patch.

In embodiments, formulation 2 can additionally provide quantitative benefits for the regulation of sleep and increased energy during awake periods.

In embodiments, formulation 2 can prevent leaky-gut syndrome, which can be a result of celiac disease.

Formulation 3

In embodiments, the third formulation can have 4 weight percent to 10 weight percent glutathione, 47 weight percent to 56 weight percent water, 3 weight percent to 9 weight percent sodium bicarbonate 1, weight percent to 5 weight percent polyoxyethylene sorbitan monooleate, 2 weight percent to 5 weight percent ascorbic acid, and 4 weight percent to 10 weight percent dimethyl sulfoxide.

In embodiments, formulation 3 can include 1 weight percent to 5 weight percent arnica.

In embodiments, formulation 3 can provide improved concentration during awake periods and reduction of joint and muscular pain and increase the ability of skin to retain moisture and totally absorb the glutathione without requiring injections or oral supplementation by at least 10 percent while the formulation is on the skin either as a transdermal delivery cream or a latex-free hypoallergenic adhesive patch.

In embodiments, the effects of the third formulation can continue for at least 24 hours while the skin is still absorbing the formulation and continues to affect the body for at least 3 days and up to 6 days depending upon the age of the individual.

Formulation 3—Example 1

John is 72 years old and weighs 185 pounds and has terrible joint pains in his knees and legs. He also tends to bruise quite easily. John has difficulty climbing stairs and walking for long periods of time. The right knee is worse than the left knee. His bruises are a deep hemorrhagic purple presentation.

The latex-free hypoallergenic adhesive patch of formulation 3 can use the following weight percents: 6 weight percent glutathione 3.5 weight percent sodium bicarbonate, 56.5 weight percent water, 3 weight percent polyoyethylene sorbitan monooleate, 3 weight percent ascorbic acid, 6 weight percent dimethyl sulfoxide, and 3 weight percent arnica.

The latex-free hypoallergenic adhesive patch was applied to John's left upper arm for 46 hours.

The latex-free hypoallergenic adhesive patch was removed after 46 hours at approximately 6:00 am. John reported that his bruising had subsided by 50 percent in presentation, and he felt a 30 percent improvement specifically to the right knee and leg. John felt that it was easier to climb stairs. Overall, there was a general reduction in pain.

Formulation 3—Example 2

David is 29 years of age, an athlete, and trains five days per week. He often will feel sore and is bruised. David has been experiencing difficulty after training since his leg tendon injury two months before. The soreness is from the lower torso down. The pulled tendon is on the left leg.

The transdermal delivery cream of formulation 3 can use the following weight percents: 5 weight percent glutathione, 3.5 weight percent sodium bicarbonate, 56.5 weight percent water, 2 weight percent polyoyethylene sorbitan monooleate, 2 weight percent ascorbic acid, 4 weight percent dimethyl sulfoxide, 5 weight percent arnica, and 3 weight percent aloe.

The transdermal delivery cream was applied to David's affected legs and upper shoulders for a total of 48 hours. He applied the transdermal delivery cream after training at 11:00 am each day and before going to bed each night at 11:00 pm.

Within 20 minutes of the applying the transdermal delivery cream. David reported that there was immediate relief by 50 percent on the left leg specifically and an overall general reduction in stiffness and tearing pain. He noted that the pain had reduced before going into training on the second day. David's overall pain, tightness and stiffness significantly reduced to 75 percent on the second day after applying the transdermal delivery cream.

Formulation 3—Example 3

Michael is 38 years of age and is a construction worker. He has persistent bruising along his wrist and elbow pain on both sides.

The latex-free hypoallergenic adhesive patch of formulation 3 can use the following weight percents: 10 weight percent glutathione, 15 weight percent sodium bicarbonate, 61.5 weight percent water, 5 weight percent polyoyethylene sorbitan monooleate, 5 weight percent ascorbic acid, 5 weight percent dimethyl sulfoxide, and 4 weight percent arnica.

The latex-free hypoallergenic adhesive patch was applied to Michael at 10:00 pm for 48 hours.

The latex-free hypoallergenic adhesive patch was removed 48 hours later. Michael reported that the first night on retiring to sleep, his stiffness and overall soreness was 50 percent better and turning and moving in bed was easier. He woke up refreshed and his wrists were 30 percent better and the bruising on the arms had subsided in color by 25 percent. The second night, Michael did not feel stiffness or pain at all while sleeping. When he woke up, he noticed that his wrists were better by 70 percent. He experienced easier flexibility and range of motion. He noted that his bruising had subsided by 60 percent.

Turning now to the Figures, FIG. 1 depicts a transdermal delivery system according to one or more embodiments.

The transdermal delivery system 10 can be applied to a user 11. While the transdermal delivery system 10 is shown attached to the user's forearm, it is understood that the transdermal delivery system can be attached to other areas of the user's body.

In embodiments, the transdermal delivery system 10 can be in the form of a latex-free hypoallergenic adhesive patch 12, which can have a layer of the formulation 14, such as in the center of the latex-free hypoallergenic adhesive patch 12.

FIG. 2 depicts a detail of the latex-free hypoallergenic adhesive patch according to one or more embodiments.

The latex-free hypoallergenic adhesive patch 12 can have a backing layer 19, which can be a thin film polymer that can be waterproof and hypoallergenic.

In embodiments, portions of an adhesive 16a and 16b can be positioned on the backing layer 19, such as on opposing edges but on the same side as the layer of the formulation 14.

In embodiments, a plurality of offset strips of magnesium glycinate 20a, 20b, and 20c can be disposed on the layer of the formulation 14.

Formulation 4

FIG. 3 depicts Formulation 4.

When Formulation 4 is placed upon an arm, transdermal Formulation 4 greatly increases the mental focus in both men and women of all ages within a time span of one hour. It will continue to help achieve clarity and focus for up to 48 hours at a time.

Formulation 5

FIG. 4 depicts Formulation 5. Formulation 5 can be applied as a transdermal cream or a gel to the skin for anti-aging as it actively starts to repair the elasticity to the face by 10 percent in the first 24 hours followed by a 10 percent reduction each day following with the reduction of wrinkles around the eyes.

Formulation 6

FIG. 5 depicts Formulation 6. Formulation 6 applied a cream is excellent for bruising, muscle pain and acute injuries. Formulation 6 will reduce inflammation within 20 minutes of the application and pain will reduce within 20 minutes of application leading to a 60 percent reduction in discoloration of the bruise within 24 hours.

Formulation 7

FIG. 6 depicts Formulation 7. Formulation 7 applied as a cream or a gel aids in constipation and the reversal of issues pertaining to the gut; such as difficulty with stool, hemorrhoids and acid-reflux. Rectal bleeding should reverse itself within 24-48 hours. Acid-reflux will reduce within two hours of the application and should repair itself over the course of two weeks by 75 percent. Constipation will reverse within 12 hours.

Formulation 8

FIG. 7 depict Formulation 8. Within 24 hours of daily and nightly application of the cream to elderly individuals. Formulation 8 will help individuals fall asleep within 30 minutes and will help individuals stay asleep throughout the night. The moisture should be 30 percent better within first 24 hours of using the topical cream which goes into the blood stream similar to the patch. Wrinkles will subside by 15 percent within the first 48 hours of use.

Formulation 9

FIG. 8 depicts Formulation 9. Formulation 9 as a liposomal cream works for the elderly and youth who injure themselves. Once the application of the cream is applied, reduction of pain by 35 percent will occur within 2 hours of use. Inflammation will subside by 50 percent in 24 hour use. Formulation 9 enters the blood stream on application and will accelerate the healing process by clearing up the bruising within 48 hours.

Formulation 10

FIG. 9 depicts Formulation 10. Formulation 10 is for both men and women who struggle with insomnia. Once the transdermal patch is applied, people will fall asleep more easily within 20 minutes of application and will sleep continuously sleep for a consecutive five hours without interruption.

Formulation 11

FIG. 10 depicts Formulation 11. Once the transdermal patch is applied, Formulation 11 reduces the effects from alcohol by 25 percent within 12 hours of intake. Also, Formulation 11 increases energy and focus the following day. Reduction of puffiness in the face from stimulants is reduced by 30 percent the following day and abdominal inflammation is reduced by 20 percent the following day after consuming stimulants.

Formulation 12

FIG. 11 depicts Formulation 12. Formulation 12 aids in the reduction of chronic headaches by 40 percent after applying a transdermal patch or gel. Reduction of migraine pain is reduced within one hour by 25 percent and headache pain by 70 percent within one hour of application. It reduces recurring migraine pain from four hours to two hours then to 20 minutes.

Formulation 13

FIG. 12 depicts Formulation 13. Formulation 13 can help with those with neurological issues such as Parkinson's. Many studies have shown that those with neurological issues have virtually no glutathione and greatly lack Vitamin D in the body. Mary is 62 and weighs 125 pounds before the application of the transdermal patch, her gait was heavily staggered, after wearing the patch, her gait reversed and it allowed her to walk comfortably without a walker within the time span of 30 minutes. Jack who is 74 with Parkinson's, weight 180 pounds, after wearing the patch his gait reversed by 50 percent within one hour. Although he still needed a walker, he walked more comfortably.

Formulation 14

FIG. 13 depicts Formulation 14.
Phase A: In a suitable tank or vessel, add 54.55 weight percent of purified water. Start heating to 80° C. Into a separate suitable container, disperse xanthan gum in glycerine. Then, add it into water while mixing at medium speed. Continue heating to 80° C.
Phase B: Into another mixing vessel, mix 3 weight percent of isopropyle myristate, 6 weight percent cetearyl oliviate, 3 weight percent caprylic/capric triglycerides, 3.5 weight percent stearyl alcohol, 3 weight percent cetyl alcohol, 2 weight percent *Helianthus annuus* (sunflower) seed oil, and 5 weight percent soy lecithin of Phase B in order. After all ingredients are added, turn the propeller on at low to medium speed. Continue mixing and heating to 75-80° C.
Once the temperatures of phases A B are attained, using transfer pump, add phase B (Oil phase) into phase A (water phase) while mixing continuously at 2000-2500 rpm with the mixer. Mix for 5 minutes.
Start cooling the batch to 50° C., Then turn the propeller to LOW speed and keep the scraper at LOW speed. Turn on chiller while continue mixing until the temperature drops to 50° C.
Phase C: Prepare premix of 6 weight percent of purified water and 5 weight percent of glutathione. At 50° C., add phase C premix into the batch, part by part, while mixing at 2500-3000 rpm speed. Mix for 10 minutes.
Phase D: At 50° C., add 0.5 weight percent essential oil into the batch slowly while mixing at medium speed. Mix for 10 minutes.
Phase E: Prepare premix of 3 weight percent water and 1.5 weight percent geogard ultra and add it into the hatch at 50° C. Then, add 0.3 weight percent glyceryl caprylate into the batch while mixing at 2500-3000 rpm speed. Mix for 10 minutes.
Start cooling the batch to room temperature while mixing continuously at 2500-3000 rpm speed. When temperature drops to 40° C., turn off the mixer and continue cooling the batch to room temperature while mixing with low speed scraper. Check and record initial pH. The pH should range from 3.5-4.5.
Formulation 14 as a liposomal cream works for individuals who are experiencing scrofulous eczema on the face. Once the application of the cream is applied, there is a reduction of oozing and itching by 25 percent within the first hour of application. The desquamation of the skin subsides by 40 percent of the use for 76 hours, offering the individual a reduced state of burning and discharged crust formation often as a result from the itching. The eczema subsides overall by 50 percent within the first 7 days of application.

Formulation 15

FIG. 14 depicts Formulation 15.
Phase A: In a suitable tank or vessel, add 49.550 weight percent of purified water. Start heating to 80° C. Into a separate suitable container, disperse 0.65 weight percent xanthan gum in 3 weight percent glycerine. Then, add it into water while mixing at medium speed. Continue heating to 80° C.

Phase B: Into another mixing vessel, mix 3 weight percent of isopropyle myristate blended, 6 weight percent cetearyl oliviate, 3.5 weight percent caprylic/capric triglycerides, 3.5 weight percent stearyl alcohol, 3 weight percent cetyl alcohol, 5 weight percent of arnica montana oil, 2 weight percent *helianthus annuus* seed oil, and 5 weight percent soy lecithin in order. After all ingredients are added, turn propeller on at low to medium speed. Continue mixing and heating to 75-80° C.

Once the temperatures of phases A & B are attained, using transfer pump, add phase B (Oil phase) into phase A (water phase) while mixing continuously at 2000-2500 rpm with the mixer. Mix for 5 minutes.

Start cooling the batch to 50° C. Then turn the propeller to LOW speed and keep the scraper at LOW speed. Turn on chiller while continuously mixing until the temperature drops to 50° C.

Phase C: Prepare premix of 6 weight percent of purified water and 5 weight percent of glutathione. At 50° C., add phase C premix into the hatch slowly, part by part while mixing at medium speed. Mix for 10 minutes.

Phase D: At 50° C., add 0.5 weight percent essential oil into the hatch, part by part, while mixing at 2500-3000 rpm speed. Mix for 10 minutes.

Phase E: Prepare premix of 3 weight percent water and 1.5 weight percent geogard ultra and add it into the batch at 50° C. Then, add 0.3 weight percent glyceryl caprylate into the batch while mixing at 2500-3000 rpm speed. Mix for 10 minutes.

Start cooling the batch to room temperature while mixing continuously at 2500-3000 rpm speed.

When temperature drops to 40° C., turn off the mixer and continue cooling the batch to room temperature while mixing with low speed scraper. Check and record initial pH. The pH can range from 3.5-4.5.

Formulation 15 as a liposomal cream works for post-surgical scarring. Once the application of the cream is applied, the redness and permeated presentation reduces by 15 percent within the first 24 hours. Over the course of applied cream for one month, the scaring on the affected part reduces by 80 percent allowing the individual to have a returned state of healthier skin presentation.

Formulation 16

FIG. 15 depicts Formulation 16.

Phase A: in a suitable tank or vessel, add 49.550 weight percent of purified water. Start heating to 80° C. Into a separate suitable container, disperse 0.6 weight percent xanthan gum in 3 weight percent glycerine. Then, add it into water while mixing at medium speed. Continue heating to 80° C.

Phase B: Into another mixing vessel, mix 3.5 weight percent of isopropyle myristate, 6 weight percent cetearyl oliviate, 3.5 weight percent caprylic, 3 weight percent stearyl alcohol, 3.5 weight percent cetyl alcohol, 2 weight percent of arnica montana oil, 2.05 weight percent *helianthus annuus* seed oil, and 5 weight percent soy lecithin in order. After all ingredients are added, turn propeller on at low to medium speed. Continue mixing and heating to 75-80° C.

Once the temperatures of phases A & B are attained, using transfer pump, add phase B phase) into phase A (water phase) while mixing continuously at 2000-2500 rpm with the mixer. Mix for 5 minutes.

Start cooling the batch to 50° C. Then turn the propeller to LOW speed and keep the scraper at LOW speed. Turn on chiller while continue mixing until the temperature drops to 50"C.

Phase C: Prepare premix of 6 weight percent of purified water and 7 weight percent glutathione. At 50° C., add phase C premix into the batch slowly, part by part while mixing at medium speed. Mix for 10 minutes.

Phase D: At 50° C., add 0.5 weight percent essential oil into the batch, part by part, while mixing at 2500-3000 rpm speed. Mix for 10 minutes.

Phase E: Prepare premix of 3 weight percent water and 1.5 weight percent geogard ultra and add it into the batch at 50° C. Then, add 0.3 weight percent glyceryl caprylate into the batch while mixing at 2500-3000 rpm speed. Mix for 10 minutes.

Start cooling the batch to room temperature while mixing continuously at 2500-3000 rpm speed.

When temperature drops to 40° C., turn off the mixer and continue cooling the batch to room temperature while mixing with low speed scraper. Check & record initial pH. The pH can range from 3.5-4.5.

Formulation 16 as a liposomal cream works for the elderly who are experiencing insomnia. Once the application of the cream is applied, an hour before bed, the ability to fall asleep will increase 35 percent will occur within 2 hours of use. The ability to sleep through the night will increase by 50 percent in first night of an eight hour sleep. This formula enters the blood stream on application.

Formulation 17

FIG. 16 depicts Formulation 17.

Phase A: in a suitable tank or vessel, add 52.550 weight percent of purified water. Start heating to 80° C. Into a separate suitable container, disperse 0.65 weight percent xanthan gum in 3 weight percent glycerine. Then, add it into water while mixing at medium speed. Continue heating to 80° C.

Phase B: Into another mixing vessel, mix has 3 weight percent of isopropyle myristate, 6 weight percent cetearyl oliviate, 3 weight percent caprylic/capric triglycerides, 3.5 weight percent stearyl alcohol, 3.2 weight percent cetyl alcohol, 3.80 weight percent *helianthus annuus* seed oil, and 4 weight percent soy lecithin of Phase B in order. After all ingredients are added, turn the propeller on at low to medium speed. Continue mixing and heating to 75-80° C.

Once the temperatures of phases A & B are attained, using transfer pump, add phase B (Oil phase) into phase A (water phase) while mixing continuously at 2000-2500 rpm with the mixer. Mix for 5 minutes.

Start cooling the batch to 50° C. Then turn the propeller to LOW speed and keep the scraper at LOW speed. Turn on chiller while continue mixing until the temperature drops to 50° C.

Phase C: Prepare premix of 6 weight percent of purified water and 6 weight percent of glutathione. At 50° C. add phase C premix into the batch, part by part, while mixing at 2500-3000 rpm speed. Mix for 10 minutes.

Phase D: At 50° C., add 0.5 weight percent essential oil into the batch slowly while mixing at medium speed. Mix for 10 minutes.

Phase B: Prepare premix of 3 weight percent water and 1.5 weight percent geogard ultra and add it into the batch at 50° C. Then, add 0.3 weight percent glyceryl caprylate into the batch while mixing at 2500-3000 rpm speed. Mix for 10 minutes.

Start cooling the batch to room temperature while mixing continuously at 2500-3000 rpm speed. When temperature drops to 40° C., turn off the mixer and continue cooling the batch to room temperature while mixing with low speed scraper. Check and record initial pH. The pH should range from 15-4.5.

Formula 17 as a liposomal cream works for teenagers who are experiencing severe acne. Once the application of the cream is applied on the face, a reduction of cystic pimples starts to decrease by 35 percent within the first 48 hours of use while the reduction of white heads start to reduce by 45 percent. Over the course of two weeks, there is a reduction of acne by 75 percent of the total face of the teenager and there is a reduction of recurring cystic pimples.

While these embodiments have been described with emphasis on the embodiments, it should be understood that within the scope of the appended claims, the embodiments might be practiced other than as specifically described herein.

What is claimed is:

1. A transdermal formulation comprising:
   a. 4 weight percent to 10 weight percent glutathione;
   b. 0.5 weight percent to 1 weight percent Vitamin D;
   c. 18 weight percent to 20 weight percent glycol;
   d. 3 weight percent to 9 weight percent sodium bicarbonate; and
   e. 47 weight percent to 58 weight percent base cream.

2. The transdermal formulation of claim 1, wherein the glycol is a propylene glycol.

3. The transdermal formulation of claim 1, wherein the glycol is at least one of: polyethylene glycol distearate, polyethylene glycol monoalkylate, polyethylene glycol monostearate, and polyethylene glycol monolaurate.

4. The transdermal formulation of claim 1, wherein the glycol is at least one of: glycerin, glycerol monocapryate, glycerol monooleate, glycerol monostearate, glycerol tri 2-ethylhexanoate.

5. The transdermal formulation of claim 1, comprising: 1 weight percent polyoxyethylene sorbitan monooleate.

6. The transdermal formulation of claim 1, further comprising weight percent to 5 weight percent arnica.

7. The transdermal formulation of claim 1, wherein the carrier of the cream has a dosage amount which creates in the patient (i) regulation of sleep, (ii) increased energy during awake periods, (iii) improved concentration during awake periods, (iv) reduction of facial wrinkles, and (v) reduction of joint and muscular pain with increases by at least 10 percent of the ability of skin to retain moisture and totally absorb the glutathione without requiring an injection or oral supplementation of the glutathione.

8. The transdermal formulation of claim 1, further applied to a latex-free hypoallergenic adhesive patch comprising:
   a. a formulation side and a back side, wherein a therapeutically effective amount of the transdermal formulation is disposed on the formulation side of the latex-free hypoallergenic adhesive patch; and
   b. a strip of magnesium glycinate attached to the transdermal formulation, wherein a dosage amount of the transdermal formulation is placed on the latex-free hypoallergenic adhesive patch for delivery to a patient over a unit of time for at least 24 hours to 48 hours; and wherein the dosage amount creates in the patient (i) regulation of sleep; (ii) increased energy during awake periods, (iii) improved concentration during awake periods, (iv) reduction of facial wrinkles, and (v) reduction of joint and muscular pain with increases by at least 10 percent of the ability of skin to retain moisture and totally absorb the glutathione without requiring an injection or an oral supplementation of the glutathione.

9. The transdermal formulation of claim 8, wherein the latex-free hypoallergenic adhesive patch is waterproof.

10. The transdermal formulation of claim 8, wherein the strip of magnesium glycinate is a continuous strip extending from one side of the transdermal formulation to the other side of the transdermal formulation.

11. The transdermal formulation of claim 8, wherein the strip of magnesium glycinate is a series of strips, which are offset from each other.

12. A transdermal formulation comprising:
   a. 4 weight percent to 10 weight percent glutathione;
   b. 75 weight percent to 85 weight percent water;
   c. 3 weight percent to 4 weight percent sodium bicarbonate; and
   d. 0.1 weight percent to 1 weight percent propylene glycol.

13. The transdermal formulation of claim 12, comprising a carrier of a cream, a gel, or a foam.

14. The transdermal formulation of claim 12, further comprising 1 weight percent to 5 percent arnica.

15. The transdermal formulation of claim 12, further applied to a latex-free hypoallergenic adhesive patch comprising:
   a. a formulation side and a back side, wherein a therapeutically effective amount of the transdermal formulation is disposed on the formulation side of the latex-free hypoallergenic adhesive patch; and
   b. a strip of magnesium glycinate is attached to the transdermal formulation, wherein a dosage amount of the transdermal formulation is placed on the latex-free hypoallergenic adhesive patch for delivery to a patient over a unit of time for at least 24 hours to 48 hours; and wherein the dosage amount creates in the patient (i) regulation of sleep, (ii) increased energy during awake periods, (iii) improved concentration during awake periods, (iv) reduction of facial wrinkles, and (v) reduction of joint and muscular pain with increases by at least 10 percent of the ability of skin to retain moisture and totally absorb the glutathione without requiring an injection or an oral supplementation of the glutathione.

16. The transdermal formulation of claim 15, wherein the latex-free hypoallergenic adhesive patch is waterproof.

17. The transdermal formulation of claim 15, wherein the strip of magnesium glycinate is a continuous strip extending from one side of the transdermal formulation to the other side of the transdermal formulation.

18. The transdermal formulation of claim 15, wherein the strip of magnesium glycinate is a series of strips which are offset from each other.

19. A transdermal formulation comprising:
   a. 4 weight percent to 10 weight percent glutathione;
   b. 47 weight percent to 56 weight percent water;
   c. weight percent to 9 weight percent sodium bicarbonate;
   d. 1 weight percent to 5 weight percent polyoxyethylene sorbitan monooleate;
   e. 2 weight percent to 5 weight percent ascorbic acid; and
   f. 4 weight percent to 10 weight percent dimethyl sulfoxide.

20. The transdermal formulation of claim 19, wherein a carrier is at least one of: a cream, a gel, or a foam.

21. The transdermal formulation of claim 19, further applied to a latex-free hypoallergenic adhesive patch, comprising:

a. a formulation side and a back side, wherein a therapeutically effective amount of the transdermal formulation is disposed on the formulation side of the latex-free hypoallergenic adhesive patch; and b. a strip of magnesium glycinate attached to the transdermal formulation, wherein a dosage amount of the transdermal formulation is placed on the latex-free hypoallergenic adhesive patch for delivery to a patient over a unit of time for at least 24 hours to 48 hours; and wherein the dosage amount creates in the patient (i) regulation of sleep, (ii) increased energy during awake periods, (iii) improved concentration during awake periods, (iv) reduction of facial wrinkles, and (v) reduction of joint and muscular pain with increases by at least 10 percent of the ability of skin to retain moisture and totally absorb the glutathione without requiring an injection or an oral supplementation of the glutathione.

22. The transdermal formulation of claim 21, wherein the latex-free hypoallergenic adhesive patch is waterproof.

23. The transdermal formulation of claim 21, wherein the strip of magnesium glycinate is a continuous strip extending from one side of the transdermal formulation to the other side of the transdermal formulation.

24. The transdermal formulation of claim 21, wherein the strip of magnesium glycinate is a series of strips which are offset from each other.

25. The transdermal formulation of claim 21, further comprising 1 weight percent to 5 weight percent arnica.

\* \* \* \* \*